US011644435B2

(12) United States Patent
Xiao et al.

(10) Patent No.: US 11,644,435 B2
(45) Date of Patent: May 9, 2023

(54) VERTICAL NANOPORE COUPLED WITH A PAIR OF TRANSVERSE ELECTRODES HAVING A UNIFORM ULTRASMALL NANOGAP FOR DNA SEQUENCING

(71) Applicant: SEAGATE TECHNOLOGY LLC, Fremont, CA (US)

(72) Inventors: ShuaiGang Xiao, Fremont, CA (US);
David S. Kuo, Palo Alto, CA (US);
Xiaomin Yang, Livermore, CA (US);
Kim Yang Lee, Fremont, CA (US);
Yautzong Hsu, Fremont, CA (US);
Michael R. Feldbaum, San Jose, CA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 474 days.

(21) Appl. No.: 16/845,565

(22) Filed: Apr. 10, 2020

(65) Prior Publication Data

US 2020/0240947 A1 Jul. 30, 2020

Related U.S. Application Data

(62) Division of application No. 15/886,723, filed on Feb. 1, 2018, now abandoned.
(Continued)

(51) Int. Cl.
*G01R 27/08* (2006.01)
*G01N 27/327* (2006.01)
(Continued)

(52) U.S. Cl.
CPC .... *G01N 27/3278* (2013.01); *B01L 3/502707* (2013.01); *B01L 3/502715* (2013.01);
(Continued)

(58) Field of Classification Search
CPC ........... G01N 27/3278; G01N 27/4145; G01N 27/4146; G01N 27/44791;
(Continued)

(56) References Cited

U.S. PATENT DOCUMENTS 5,007,984 A 4/1991 Tsutsumi et al.
5,071,714 A 12/1991 Rodbell et al.
(Continued)

FOREIGN PATENT DOCUMENTS

WO 2004077503 A1 10/2004
WO 2015057870 A1 4/2015

OTHER PUBLICATIONS

Ohshiro, Takahito et al., "Single-Molecule Tunnel-Current Based Identification of DNA/RNA Towards Sequencing by Using Nano-MDBJ," 16th International Conference on Miniaturized Systems for Chemistry and Life Sciences, pp. 204-206, Oct. 28-Nov. 1, 2012.
(Continued)

*Primary Examiner* — Thang X Le
(74) *Attorney, Agent, or Firm* — Holzer Patel Drennan

(57) ABSTRACT

A DNA sequencing device and methods of making. The device includes a pair of electrodes having a spacing of no greater than about 2 nm, the electrodes being exposed within a nanopore to measure a DNA strand passing through the nanopore. The device can be made by depositing a conductive layer over a sacrificial channel and then removing the sacrificial channel to form the electrode gap.

19 Claims, 8 Drawing Sheets

Related U.S. Application Data

(60) Provisional application No. 62/469,409, filed on Mar. 9, 2017.

(51) Int. Cl.

| | |
|---|---|
| *G01N 33/487* | (2006.01) |
| *C12Q 1/6869* | (2018.01) |
| *C23C 14/00* | (2006.01) |
| *B01L 3/00* | (2006.01) |
| *G01N 27/414* | (2006.01) |
| *G01N 27/447* | (2006.01) |
| *B82Y 5/00* | (2011.01) |

(52) U.S. Cl.
CPC ...... *B01L 3/502761* (2013.01); *C12Q 1/6869* (2013.01); *C23C 14/00* (2013.01); *G01N 27/4145* (2013.01); *G01N 27/4146* (2013.01); *G01N 27/44791* (2013.01); *G01N 33/48721* (2013.01); *B81C 2201/0143* (2013.01); *B81C 2201/0176* (2013.01); *B81C 2201/0181* (2013.01); *B82Y 5/00* (2013.01)

(58) Field of Classification Search
CPC ....... G01N 33/48721; G01N 33/48728; G01N 21/6486; C12Q 1/6869; C12Q 2563/116; C12Q 2565/607; C12Q 2565/631
See application file for complete search history.

(56) References Cited

U.S. PATENT DOCUMENTS

| | | | |
|---|---|---|---|
| 5,127,989 | A | 7/1992 | Haraguchi et al. |
| 6,627,067 | B1 | 9/2003 | Branton et al. |
| 7,416,993 | B2 | 8/2008 | Segal et al. |
| 7,582,490 | B2 | 9/2009 | Golovchenko et al. |
| 8,105,471 | B1 | 1/2012 | Han et al. |
| 9,410,923 | B2 | 8/2016 | Sauer et al. |
| 10,247,700 | B2 | 4/2019 | Hu et al. |
| 10,261,066 | B2 | 4/2019 | Ikeda et al. |
| 10,413,903 | B2 | 9/2019 | Taniguchi |
| 10,712,334 | B2 | 7/2020 | Choi et al. |
| 2002/0039737 | A1 | 4/2002 | Chan et al. |
| 2003/0141189 | A1 | 7/2003 | Lee et al. |
| 2006/0246497 | A1 | 11/2006 | Huang et al. |
| 2009/0283412 | A1 | 11/2009 | Sansinena et al. |
| 2010/0188109 | A1 | 7/2010 | Edel |
| 2010/0267158 | A1 | 10/2010 | Chou et al. |
| 2011/0174629 | A1 | 7/2011 | Bouchet et al. |
| 2011/0224098 | A1 | 9/2011 | Luan et al. |
| 2012/0037919 | A1* | 2/2012 | Xu ........................ C12Q 1/6869 257/E29.166 |
| 2012/0325664 | A1* | 12/2012 | Shim ................ G01N 33/48721 204/601 |
| 2012/0326732 | A1* | 12/2012 | Cho ................. G01N 33/48721 324/692 |
| 2013/0334047 | A1 | 12/2013 | Jeong et al. |
| 2014/0008225 | A1* | 1/2014 | Jeon ................. G01N 27/44791 204/603 |
| 2014/0045270 | A1* | 2/2014 | Shim ...................... G01N 33/50 422/69 |
| 2014/0151228 | A1 | 6/2014 | Royyuru et al. |
| 2014/0312002 | A1 | 10/2014 | Peng |
| 2014/0326954 | A1 | 11/2014 | Han et al. |
| 2016/0153105 | A1 | 6/2016 | Gumbercht |
| 2016/0319342 | A1 | 11/2016 | Kawai et al. |
| 2017/0144158 | A1 | 5/2017 | Taniguchi |
| 2017/0146510 | A1 | 5/2017 | Ikeda et al. |
| 2017/0253479 | A1 | 9/2017 | Nikoobakht, IV |
| 2018/0120287 | A1* | 5/2018 | Henck ............. G01N 27/44791 |
| 2019/0292589 | A1* | 9/2019 | Fujioka .................... C12Q 1/68 |
| 2019/0310200 | A1 | 10/2019 | Lee et al. |
| 2019/0310241 | A1* | 10/2019 | Topolancik .......... C12Q 1/6825 |

OTHER PUBLICATIONS

Di Ventra, Massimiliano, et al., "Decoding DNA, RNA and peptides with quantum tunneling," Nature Nanotechnology, vol. 11, Feb. 2016, pp. 117-126.

Feng, Yanxiao, et al., "Nanopore-based Fourth-generation DNA Sequencing Technology," Genomics Proteomics Bioinformatics, 13 (2015), pp. 4-16.

Ivanov, A.P., et al., "DNA Tunneling Detector Embedded in a Nanopore," Nano Letters, 2011, 11, pp. 279-285.

Ke, Rongqin, et al., "Fourth Generation of Next-Generation Sequencing Technologies: Promise and Consequences," Human Mutation, vol. 37, No. 12, 2016, pp. 1363-1367.

Kulski, Jerzy K., "Next-Generation Sequencing—An Overview of the History, Tools, and 'Omic' Applications," http://dx.doi.org/10.5772/61964, 2015, 59 pages.

Duan et al., "Review article: Fabrication of nanofluidic devices," Biomicrofluidics 7, 026501 (2013).

Iqbal, Samir M., et al., Nanopores, Springer, New York, US, 2011.

* cited by examiner

VERTICAL NANOPORE COUPLED WITH A PAIR OF TRANSVERSE ELECTRODES HAVING A UNIFORM ULTRASMALL NANOGAP FOR DNA SEQUENCING

RELATED APPLICATIONS

This application is a divisional application of U.S. patent application Ser. No. 15/886,723 filed Feb. 1, 2018, which claims the benefit of the filing date of U.S. Provisional Application No. 62/469,409, filed Mar. 9, 2017, and entitled VERTICAL NANOPORE COUPLED WITH A PAIR OF TRANSVERSE ELECTRODES HAVING A UNIFORM ULTRASMALL NANOGAP FOR DNA SEQUENCING, the disclosures of which are incorporated in their entirety by this reference.

SUMMARY

The present disclosure relates to design and fabrication of a new type of nanopore structure for use in DNA sequencing. The nanopore structure includes two transverse electrodes with an ultrasmall nanogap therebetween. The nanogap is exposed within the nanopore and the electrodes are operable to detect specific nucleotides of a DNA strand passing through the nanopore.

One aspect of the present disclosure relates to a nanopore DNA sequencing device that includes a nanopore having a maximum width dimension of no greater than about 50 nm, and a pair of electrodes having a spacing of no greater than about 2 nm to about 3 nm. The spacing or gap between the electrodes is exposed within the nanopore. The electrodes measure an electronic signal associated with a DNA strand passing through the nanopore.

In some embodiments, the nanopore width may be no greater than about 30 nm. The electrode spacing may be no greater than about 1 nm. The electrode spacing may be in the range of about 0.3 nm to about 2 nm. The nanopore may be oriented with a vertically upward facing inlet opening. The electrodes may have a length that is greater than the maximum width dimension of the nanopore. The spacing between the electrodes may be formed using a lithography process.

Another aspect of the present disclosure relates to a method of forming a nanopore device used for DNA sequencing. The method includes providing a substrate having a first sacrificial layer positioned thereon, the first sacrificial layer extending across a portion of a width of the substrate and having an exposed sidewall, depositing a second sacrificial layer on the substrate and the first sacrificial layer, the second sacrificial layer covering the exposed sidewall, etching the first and second sacrificial layers to form a channel deposit, forming an electrode layer on the substrate and at least partially covering the channel deposit, removing the channel deposit (e.g., using wet stripping) to form an electrode gap, depositing an insulating layer on the electrode layer, and forming a nanopore in the insulating layer in alignment with the electrode gap.

Forming the electrode layer may include using evaporation techniques. The first sacrificial layer may be a photoresist layer, and the second sacrificial layer may comprise Chromium (Cr). The second sacrificial layer may be formed by one of sputter deposition, chemical vapor deposition, and atomic layer deposition. The channel deposit may have a width in the range of about 0.3 nm to about 2 nm. Removing the channel deposit may include lifting off using wet stripping. Forming the nanopore may include drilling through the insulating layer using focused electron beam or focused ion beam techniques. Depositing the insulation coating may include depositing by isotropic deposition.

A further aspect of the present disclosure relates to a method of DNA sequencing. The method includes providing a nanopore DNA sequencing device, the nanopore DNA sequencing device comprising a nanopore and a tunneling current electrode, the tunneling current electrode comprising first and second electrode members separated by an electrode gap, the nanopore having a maximum width dimension no greater than about 50 nm, and the electrode gap being no greater than about 2 nm. The method also includes directing a DNA strand through the nanopore and the electrode gap, and measuring a tunneling current of at least one nucleotide of the DNA strand as the DNA strand passes through the electrode gap. The method may include determining a sequence of the nucleotides of the DNA strand based on the measured electronic signals, or a plurality of measured electronic signals.

The nanopore may be oriented with an inlet opening of the nanopore facing vertically upward, and the DNA strand may pass through the nanopore and electrode gap in a vertically downward direction. The maximum width dimension of the nanopore may be no greater than about 30 nm. The electrode gap may be no greater than about 1 nm. The electrode gap may be in the range of about 0.3 nm to about 2 nm. Measuring the tunneling current of the at least one nucleotide may include measuring the tunneling current of at least four different nucleotides (A,T,C,G) of the DNA strand.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

DETAILED DESCRIPTION

Figure 1:
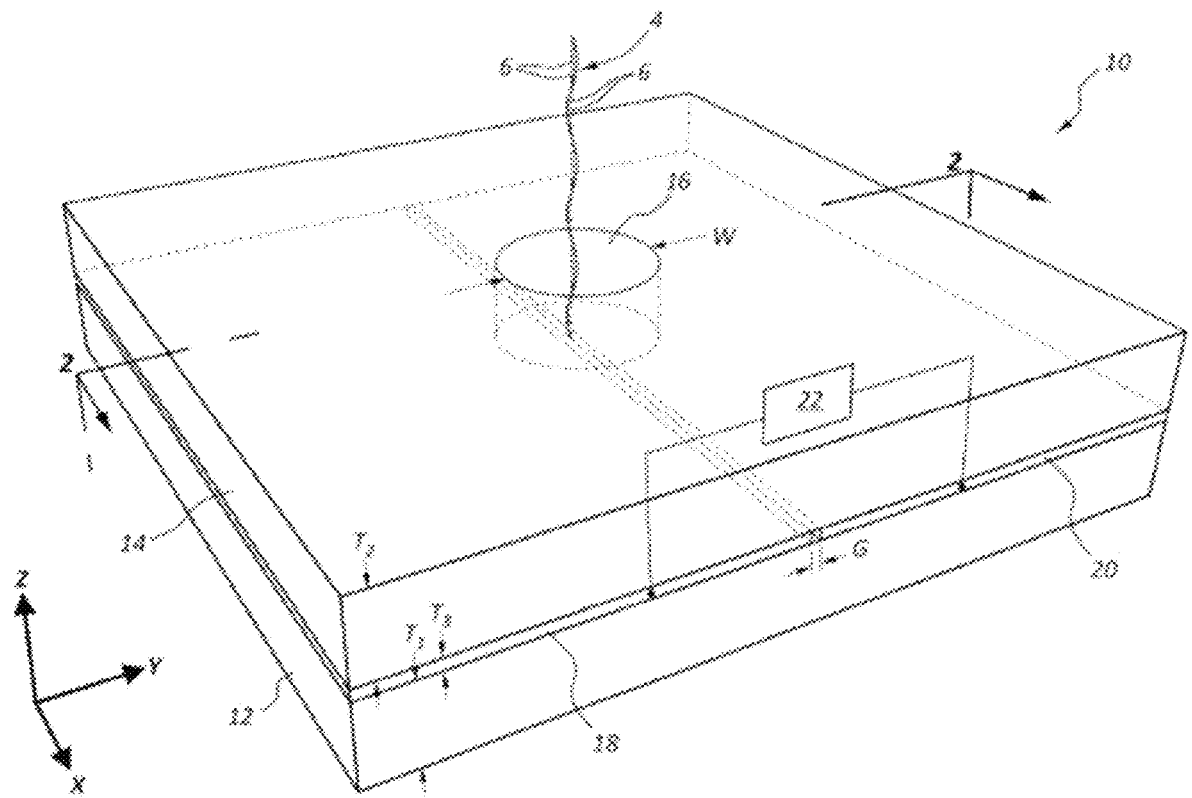
FIG. 1 shows a perspective view of an example nanopore DNA sequencing device in accordance with the present disclosure.

Despite considerable efforts, DNA sequencing today still suffers from relatively high costs and low speeds. To address these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

The present disclosure generally relates to DNA sequencing, and more particularly relates to DNA sequencing devices having nanopores and nanoelectrodes, and related methods of fabricating such devices. The present disclosure may also relate to DNA sequencing using such devices.

Direct measure of individual nucleotides of long DNA strands rapidly and with low cost is one goal of DNA sequencing. Among these options, nanopore- and nanochannel-based approaches that measure a transverse signal across individual nucleotides have emerged as a promising approach. The general approach involves electrically driving DNA and RNA strands through a nanopore or narrow channel via ionic flow or driven by a pressure gradient. As the strand passes a high resolution sensor embedded inside the channel, the high spatial resolution sensor measures the unique properties of the individual nucleotides (A,T,C,G). One type of sensor would consist of a conductive electrode that measures the unique tunneling currents associated with the nucleotide, thereby identifying and resolving the four unique nucleotide types.

However, there are several significant challenges associated with the fabrication of such devices at relatively low cost that can spatially resolve individual nucleotides of each strand, wherein nucleotides are on the order of about 1 nm is size in a transverse direction. One challenge is the ability to fabricate a channel width on the order of about 1 nm (e.g., in the range of about 0.3 nm to about 2 nm) with accuracy and repeatability to obtain tunneling current that is exponential verses distance. Such a channel or pore is sometimes referred to as a nanochannel or nanopore. For example, the signal tunneling current would reduce by a factor of about 1000× if spacing is increased between electrode and base molecule by only about 0.5 nm. A second challenge relates to fabrication of a sensor or nanoelectrode that is on the order of about 1 nm in spacing between the electrodes in order to resolve and detect individual nucleotides (e.g., A,T,C,G) in the DNA strand.

Methods are disclosed herein related to fabricating a nanochannel in a DNA sequencing device with dimensions as small as a few nanometers or less. One feature of the DNA sequencing devices formed according to such methods is the relative small nanopore for guiding the single molecule DNA to flow through. Another feature of the device is a tunneling current electrode (TCE) having an even narrower gap between the electrode members of the TCE than the size of the nanopore. The TCE gap is required to be on the order of about 1 nm in order to better detect DNA signals, and particularly in the range of about 0.3 nm to about 2 nm. The devices and methods disclosed herein may be based at least in part on a sidewall lithography process as part of forming the TCE gap.

A relatively fast and low-cost genome (DNA), transcriptome (RNA) and proteome (all proteins) sequencing method could lead to the development of personalized medicine (e.g., the ability to target drugs and medical treatments specially to an individual). However, to fabricate a nanopore for single molecular DNA sequencing is still technically challenging due to the extremely small dimensions involved with the devices used to conduct the sequencing. The devices and methods disclosed herein address at least some of these challenges.

To improve DNA sequencing throughput and lower the cost, direct-reading sequencing device like nanopore devices based on, for example, (1) semiconductor nanopore, and (2) transverse electron current measurement may be highly desirable.

A nanopore structure with a pair of transverse electrodes can be fabricated using conventional nanofabrication processes. A limitation of this structure is the wide nanogap between two electrodes defined by lithography, which is typically in the range of 10 nm to about 30 nm. Ideally a small nanogap between two electrodes on the order of about 0.3 nm and about 2 nm (more particularly on the order of about 1 nm) is preferred to enhance the signal-to-noise ratio during transverse current detection due to the ultrasmall diameter of DNA single strand (~1 nm). The present disclosure relates to a new design for a nanopore with two transverse electrodes having a uniform, ultrasmall nanogap on the order of about 1 nm (e.g., in the range of about 0.3 nm to about 2 nm). A fabrication process flow to create this nanogap structure is described as well.

Figure 8:
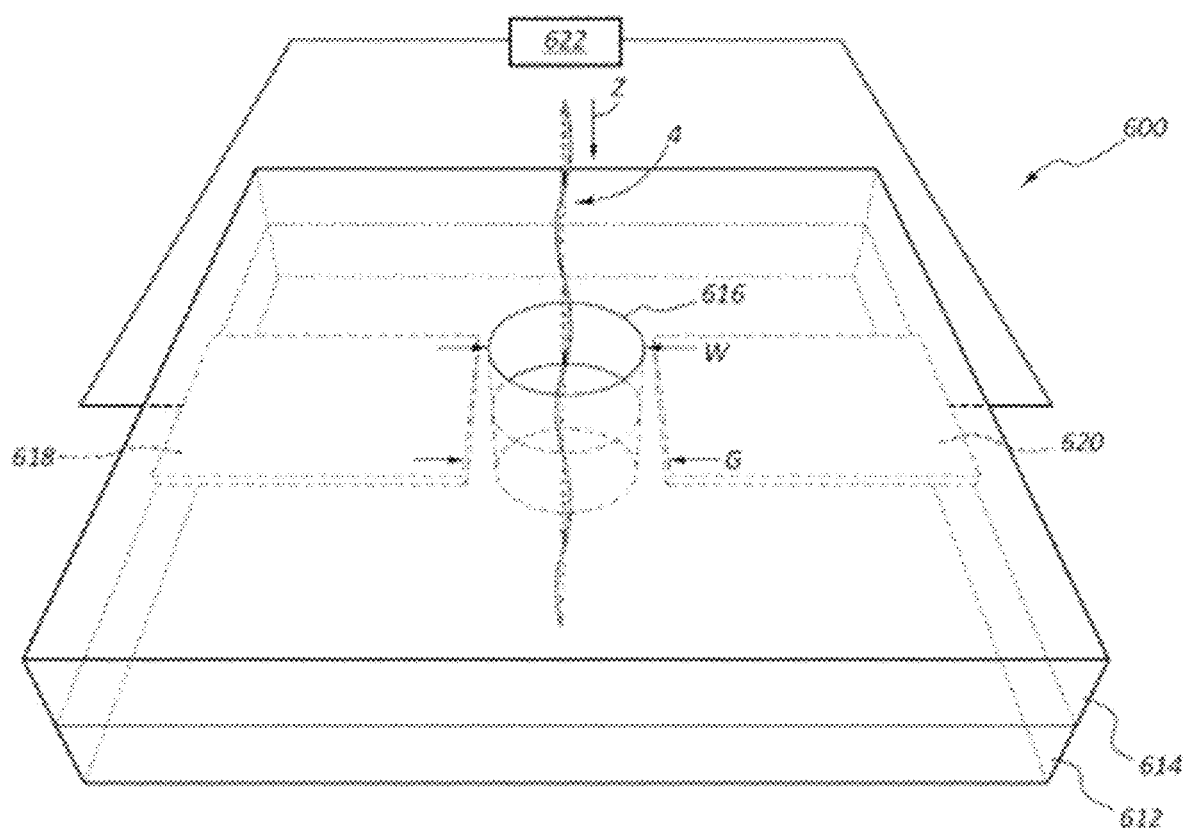
FIG. 8 is a perspective view of a nanopore DNA sequencing device according to the prior art.

FIG. 8 shows a DNA sequencing device 600 in accordance with the prior art. DNA sequencing device 600 includes a substrate 612, an upper layer 614 positioned on this substrate 612, a nanopore 616 extending through the substrate 612 and upper layer 614, and first and second electrodes 618, 620 positioned between the substrate 612 and upper layer 614. The nanopore 616 has a width W. The first and second electrodes 618, 620 are spaced apart a distance defined as a gap G. Typically, the width W is equal to or less than the gap G. Conventional nanofabrication processes may be used to create the DNA sequencing device 600. A limitation of this structure is the relatively wide nanogap between the first and second electrodes 618, 620, which is typically in the range of about 10 nm to about 50 nm, and at best in the range of about 10 nm to about 30 nm.

A smaller nanogap between the electrodes in the order of about 0.3 nm and about 2 nm (more particularly on the order of about 1 nm) may be preferred to the embodiment of the DNA sequencing device 600 to enhance the signal-to-noise ratio during transfers current detection due to the ultra-small diameter of a DNA strand, which is on the order of about 1 nm. The embodiments described with reference to FIGS. 1-3 meets the requirements of the desired smaller nanogap size.

The nanopore DNA sequencing device 600 shown in FIG. 8 may be modified according to principles of the present disclosure such that the maximum dimension of the nanopore inlet (e.g., the width W) is in the range from about 0.3 nm to about 10 nm, and more particularly in the range of about 0.3 nm to about 5 nm. The spacing or gap between the electrodes which is exposed in the nanopore passing through the upper layer and substrate is in the range of about 0.3 nm to about 2 nm.

Figure 2:
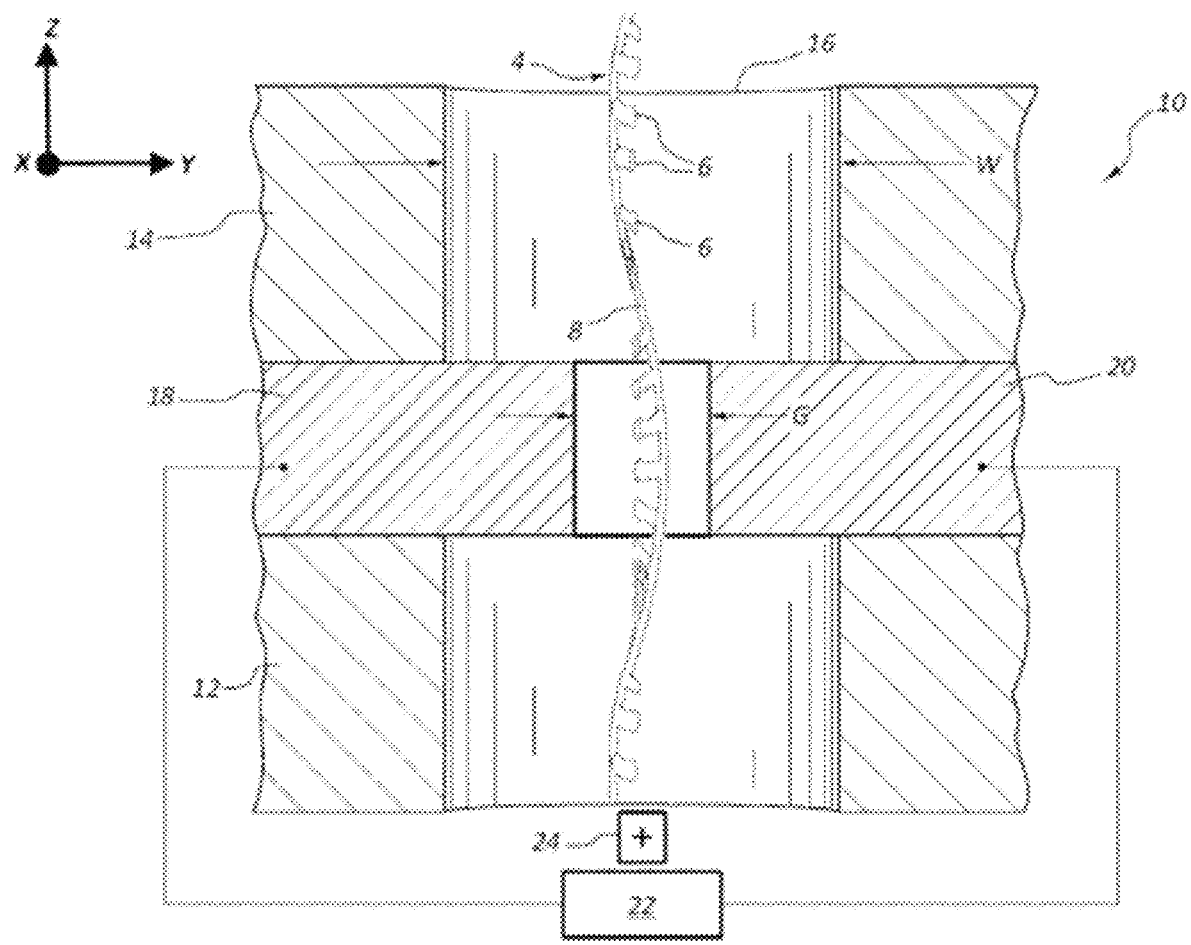
FIG. 2 shows a cross-sectional view of the nanopore DNA sequencing device of FIG. 1 taken along cross-section indicators 2-2.
Figure 4:
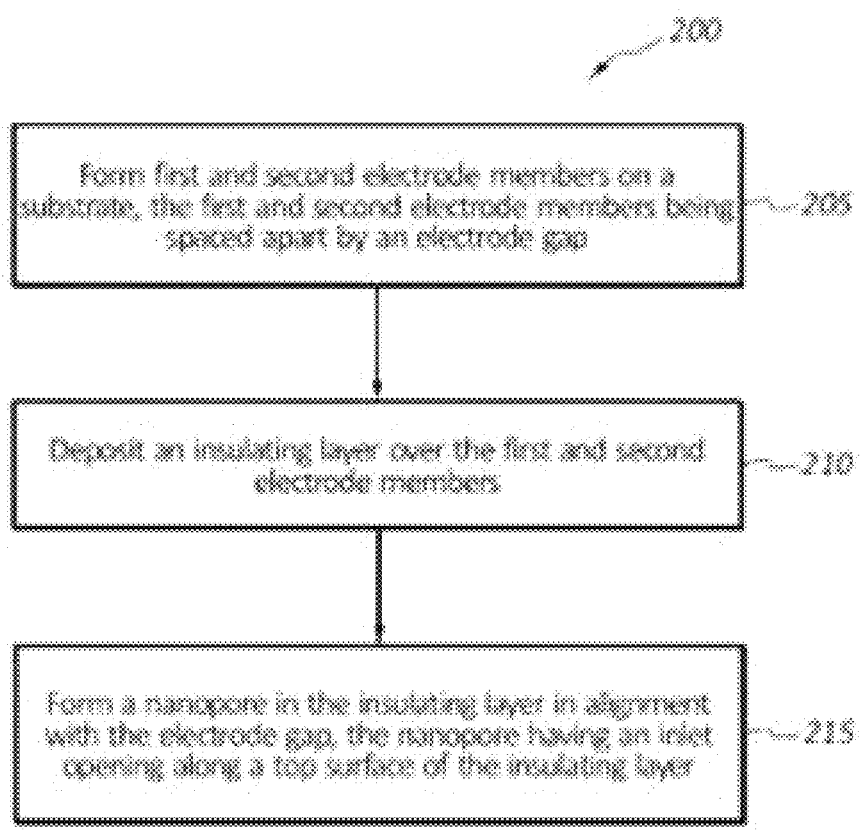
FIG. 4 is a flow diagram showing an example method in accordance with the present disclosure.
Figure 5:
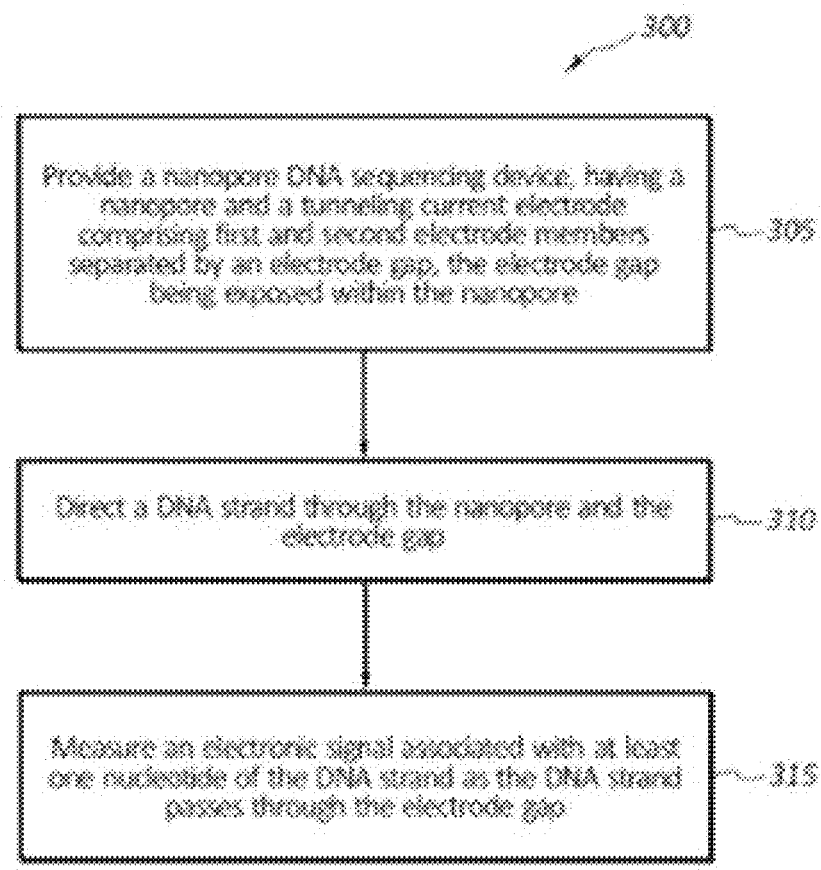
FIG. 5 is a flow diagram showing an example method in accordance with the present disclosure.
Figure 6:
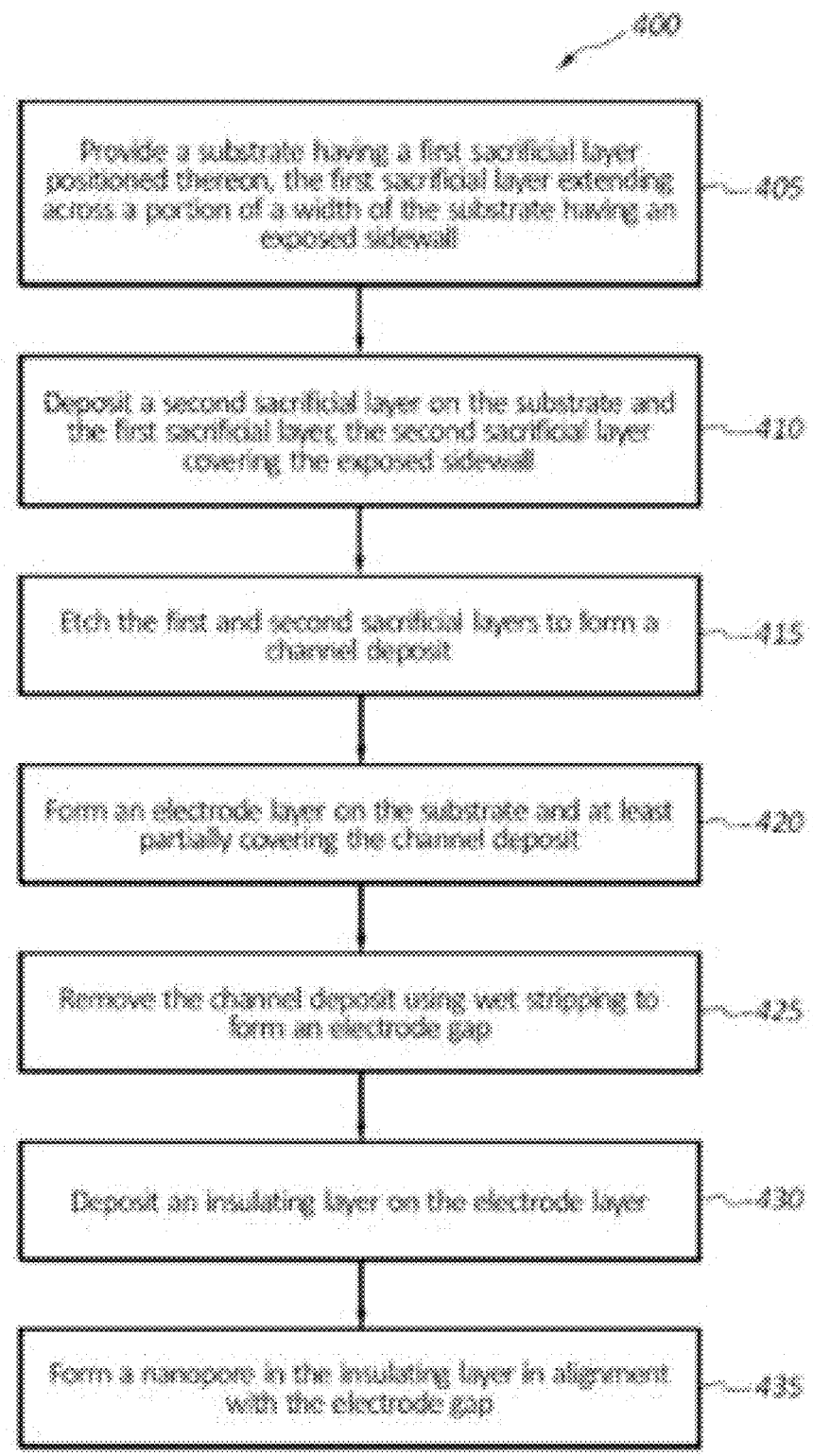
FIG. 6 is a flow diagram showing an example method in accordance with the present disclosure.

FIGS. 1 and 2 show perspective and cross-sectional side views of a nanopore DNA sequencing device 10 with two transverse electrode (TCE) and having a uniform nanogap in the range from about 0.3 nm to about 2 nm. A fabrication process flow for a structure similar to what is illustrated in FIGS. 1 and 2 is provided in FIG. 3. FIGS. 4 and 6 are flow diagrams showing example methods for fabricating a nanopore structure with a pair of transverse electrodes having a uniform ultra-small nanogap on the order of about 0.3 nm to about 2 nm using, for example, sidewall lithography techniques. Many other fabrication methods may be used to create a nanopore DNA sequencing device having similar features and functionality as the device disclosed with reference to FIGS. 1-3. FIG. 5 is a flow diagram showing an example method of DNA sequencing using the nanopore DNA sequencing device as disclosed herein.

FIGS. 1 and 2 illustrate a DNA sequencing device 10 having a substrate 12, an upper layer 14, a nanopore 16, and first and second electrodes 18, 20. The electrodes 18, 20 are coupled electronically to each other via a controller or pre-amp 22. As shown in FIG. 1, the substrate 12 has a thickness $T_1$, the upper layer 14 has a thickness $T_2$, and the first and second electrodes have thicknesses $T_3$. During a DNA sequencing process, an energy source 24 is positioned at a bottom end of the nanopore 16 to draw a DNA strand 4 into and through DNA strand and past the first and second electrodes 18, 20. The DNA strand 4 includes a plurality of nucleotides 6 mounted to a backbone 8. The nucleotides 6 include individual nucleotides (A,T,C,G), which can be distinguished between based on the electronic signal detected as the DNA strand 4 passes through the gap G between electrodes 18, 20. The DNA strand travels in the direction Z as it passes through the nanopore 16.

As shown in at least FIG. 2, the gap G between the first and second electrodes 18, 20 is less than a width W of the nanopore 16 (see FIG. 1). Fabricating the DNA sequencing device 10 in a way that the gap G is less than the nanopore width W may be accomplished using, for example, the fabrication steps shown in FIG. 3.

In one embodiment, the thickness $T_2$ is in the range of about 5 nm to about 20 nm, the thickness $T_3$ is in the range from about 0.5 nm to about 5 nm, and the thickness $T_1$ is in the range from about 5 nm to about 50 nm. The upper layer 14 may comprise, for example, an insulating material such as, for example, carbon (C), silicon oxide ($SiO_2$), or silicon nitride (SiN). The electrode layer may comprise a conductive material such as, for example, silver (Au), platinum (Pt), or Ruthenium (Ru).

The nanopore 16 may be formed using any of a variety of fabrication steps including, for example, drilling using a focused electron or ion beam. The material of the substrate 12 and upper layer 14 may have a lower atomic number than the atomic number of the material for the first and second electrodes 18, 20, thus making it easier to remove the substrate 12 and upper layer 14 as part of forming the nanopore 16.

Figure 3:
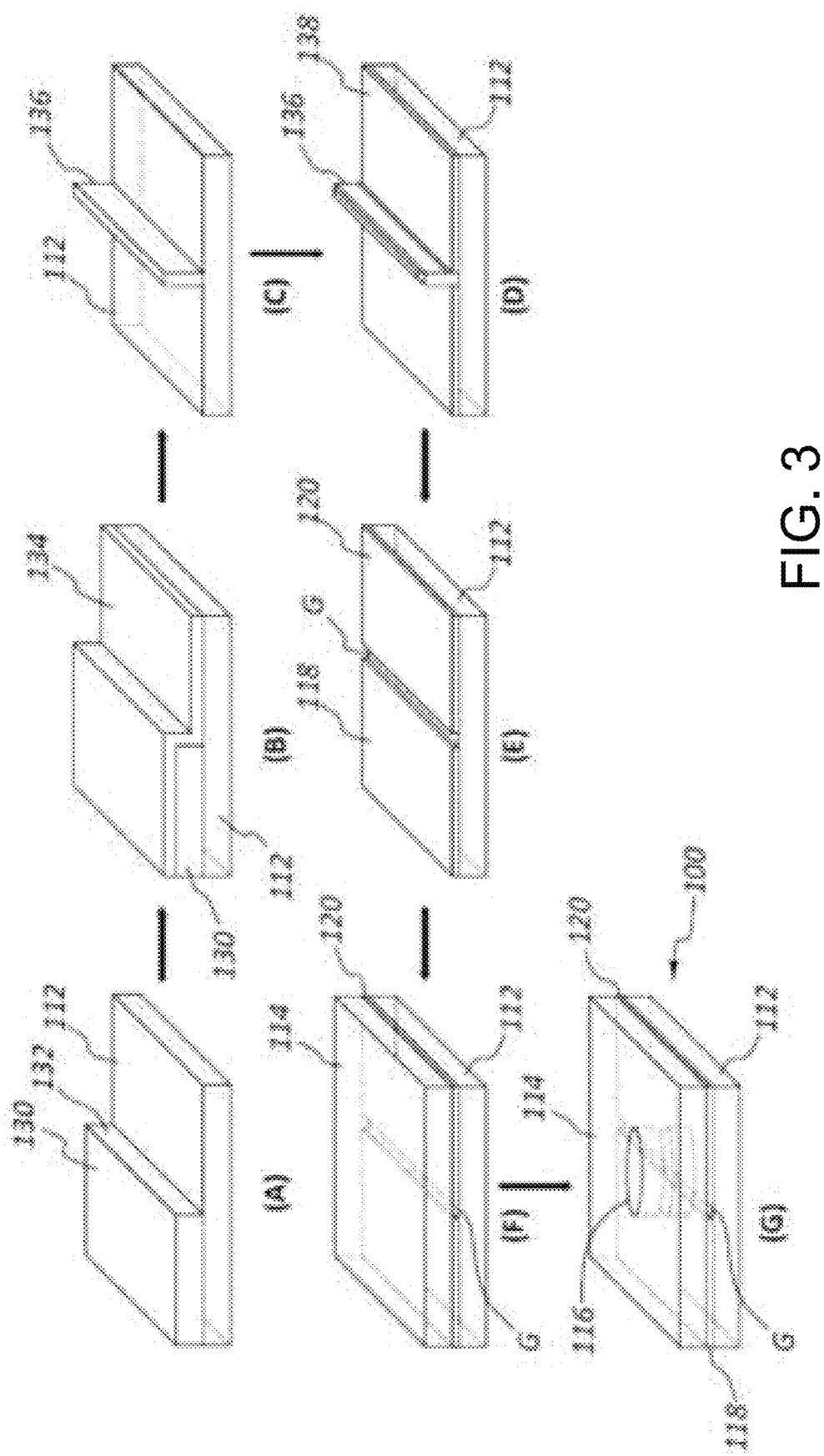
FIG. 3 shows a series of steps of an example method of fabricating a nanopore DNA sequencing device in accordance with the present disclosure.

The example fabrication process shown in FIG. 3 has an initial step of providing or forming a substrate 112 having a first sacrificial layer 130 positioned thereon. The first sacrificial layer 130 may extend across a portion of a width of the substrate 112, and provide an exposed sidewall. The first sacrificial layer 112 may comprise, for example, Carbon (C) or other photoresist material. A second sacrificial layer 134 may be deposited on the first sacrificial layer 130 and a portion of the substrate 112. The second sacrificial layer 134 may comprise, for example, Chromium (Cr) or a similar material. The second sacrificial layer 134 may cover the exposed sidewall 132.

The first and second sacrificial layers 130, 134 may be etched back to form a channel deposit 136. A further step may include forming an electrode layer 138 on the substrate 112. The electrode layer 138 may be formed by, for example, an evaporation or sputter deposition method. A further step may include lift-off of a top electrode line by wet stripping (e.g., Cr wet stripping) to remove the channel deposit 136. By removing the channel deposit 136, a pair of first and second electrodes 118, 120 remains on the substrate 112 with a gap G defined there between.

The top insulating layer 114 may be deposited on the electrode layer 138 (e.g., the first and second electrodes 118, 120). A hole may be formed in the insulating layer 114 in alignment with the channel or gap G formed in the electrode layer 138, thus resulting in the nanopore 116. Various fabrication methods may be used to form the nanopore, including, for example, focused electrode beam, ion beam, or other drilling techniques.

As described above, FIG. 8 shows a nanopore structure DNA sequencing device 600 with a pair of transverse electrodes 618, 620 that may be fabricated using conventional nanofabrication processes. A limitation of this structure is the wide nanogap between the electrodes, which is typically in the range of about 10 nm to about 50 nm, although can be in the range of about 10 nm to about 30 nm.

A smaller nanogap between two electrodes on the order of about 0.3 nm and about 2 nm (more particularly on the order of about 1 nm) may be preferred to enhance the signal-to-noise ratio during transverse current detection due to the ultrasmall diameter of DNA single strand (~1 nm).

The nanopore DNA sequencing device shown in FIG. 8 may be modified according to principles of the present disclosure such that the maximum dimension of the nanopore inlet is in the range of about 0.3 nm to about 5 nm, and the spacing or gap between the electrodes is in the range of about 0.3 nm to about 2 nm.

FIGS. 1 and 2 show perspective and cross-sectional side views of a nanopore design with two transverse electrodes (TCE) having a uniform nanogap in the range of about 0.3 nm to about 2 nm (although a range of about 0.1 to about 5 nm is contemplated and may provide certain advantages). A fabrication process flow for a structure similar to what is illustrated in FIGS. 1 and 2 is shown in FIG. 3.

FIGS. 4 and 6 are flow diagrams showing example methods for fabricating a nanopore structure with a pair of transverse electrodes having a uniform ultrasmall nanogap on the order of about 0.3 nm to about 2 nm using sidewall lithography techniques. Many other fabrication methods may be used to create a nanopore DNA sequencing device having similar features and functionality as the devices disclosed herein (e.g., those devices shown in FIGS. 1-2). FIG. 5 is a flow diagram showing an example method of DNA sequencing using the nanopore devices disclosed herein.

The following includes explanations of materials and processes that may be used in the process flow shown in FIG. 3:

Insulator layer between electrodes and substrate may be optional if the substrate is conductive.

Carbon (C)/photoresist may act as a sacrificial layer during sidewall lithography processes.

Chromium (Cr) may act as a sacrificial layer during the formation of the nanochannel in the electrode layer, may be replaced by other metallic or non-metallic materials, and may be deposited by, for example, sputter/chemical vapor deposition/atomic layer deposition, or the like.

The nanoelectrode may be formed using, for example, one of (1) sidewall lithography for gaps G the range of less than about 0.3 nm to about 2 nm, or (2) conventional (e.g., electron-beam, etc.) lithography plus either additive (e.g., liftoff, etc.) or subtractive (e.g., etching, etc.) pattern transfer processes for gaps G in the range of about 2-5 nm or less.

Chromium (Cr) removal may be done, for example, either by dry reactive ion etching (RIE) or wet chemical etch.

Deposition of insulator may include, for example, an isotropic deposition process to provide closure of the top portion of the nanochannel without filling the channel too much. This step may be optional.

Referring now to FIG. 4, an example method 200 associated with use of the DNA sequencing device as disclosed herein is provided in the form of a flow diagram. FIG. 4 illustrates example steps of a method 200 of forming a nanopore device for DNA sequencing. The method 200 may include, at block 205, the step of forming first and second electrode members on a substrate, the first and second electrode members being spaced apart by an electrode gap. At block 210, the method includes depositing an insulating over the first and second electrode members. At block 215, the method includes forming a nanopore in the insulating layer in alignment with the electrode gap, the nanopore having an inlet opening along a top surface of the insulating layer. The electrode gap may be in the range of about 0.3 nm to about 2 nm, and/or on the order of 1 nm. The inlet opening or nanopore opening may have a minimum width dimension in the range from about 10 nm to about 30 nm. Forming the first and second electrode members may include vapor evaporation techniques. Forming the electrode gap may include depositing at least one sacrificial layer using at least one of sputter deposition, chemical vapor deposition, and atomic layer deposition, and then removing a portion of the sacrificial layer. Forming the nanopore may include drilling through the insulating layer using focused electron beam or focused ion beam techniques. Depositing the insulation layer may include depositing by isotropic deposition.

FIG. 5 illustrates a method of DNA sequencing using a nanopore DNA sequencing device. The method 300 may include, at block 305, providing a nanopore DNA sequencing device having a nanopore and a tunneling current electrode comprising first and second electrode members separated by an electrode gap, wherein the electrode gap is exposed within the nanopore. Block 310 includes directing a DNA strand through the nanopore and the electrode gap. Block 315 includes measuring an electronic signal associated with at least nucleotide of the DNA strand as the DNA strand passes through the electrode gap. The method 300 may include determining a sequence of the nucleotides of the DNA strand based on the measured electronic signals, or a plurality of measured electronic signals. The method 300 may further include drawing the electrode strand through the nanopore and electrode gap using electrophoresis. The electrode gap may be in the range of about 0.3 nm to about 2 nm, or on the order of about 1 nm. The nanopore may have a maximum width in the range from about 10 nm to about 30 nm. The DNA strand may be directed vertically into the nanopore and through the electrode gap where electronic signals associated with the individual nucleotides of the DNA strand are measured.

FIG. 6 illustrates a method 400 of forming a nanopore DNA sequencing device. The method 400 may include, at block 405, providing a substrate having a first sacrificial layer positioned thereon, wherein the first sacrificial layer extends across a portion of a width of the substrate and has an exposed sidewall. Block 410 includes depositing a second sacrificial layer on the substrate and the first sacrificial layer, wherein the second sacrificial layer covers the exposed sidewall. Block 415 includes etching the first and second sacrificial layers to form a channel deposit. Block 420 includes forming an electrode layer on the substrate and at least partially covering the channel deposit. Block 425 includes removing the channel deposit using, for example, wet stripping to form an electrode gap. Block 430 includes depositing an insulating layer on the electrode layer. Block 435 includes forming a nanopore in the insulating layer in alignment with the electrode gap to create a path through the insulating layer, electrode layer, and substrate for passage of the DNA strand.

The method 400 may include providing the electrode gap with a maximum width dimension in the range from about 0.3 nm to about 2 nm. The nanopore may be formed with a maximum or minimum dimension in the range from about 10 nm to about 30 nm.

The various methods 200, 300, 400 and their associated steps may be modified or altered in accordance with the present disclosure to include more or fewer steps than those illustrated in the figures. Accordingly, the flow diagram shown in FIGS. 4-6 should not exclude any step or variation of methods relating to formation of a nanopore DNA sequencing device and/or DNA sequencing using a nanopore DNA sequencing device having the features and/or functionality described herein.

Figure 7:
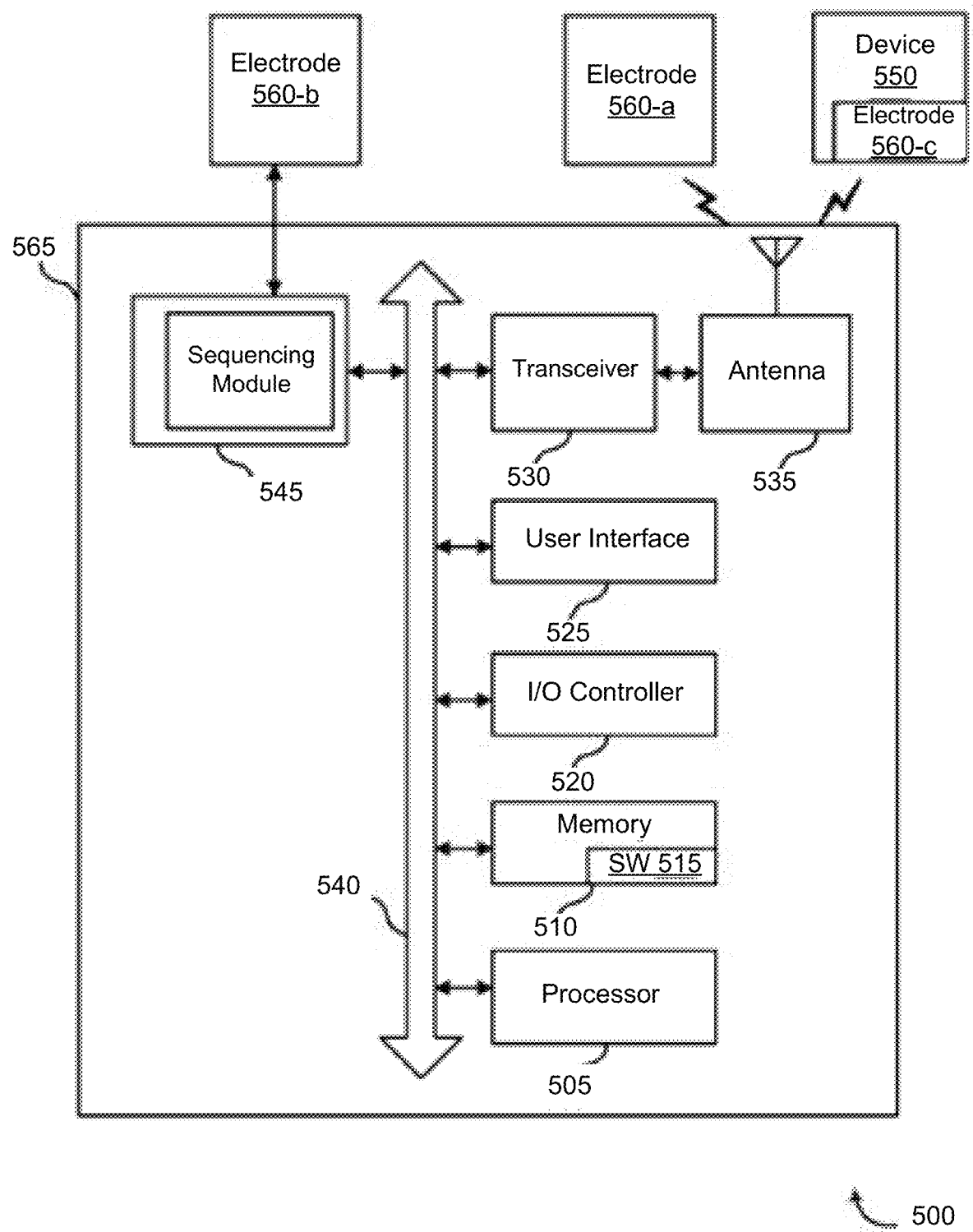
FIG. 7 shows a diagram of a system in accordance with various aspects of this disclosure.

FIG. 7 shows a system 500 for use with the DNA sequencing devices and systems shown in FIGS. 1-3. System 500 may include a control panel 565. Control panel 565 may be equivalent at least in part to a controller, control unit, processor or the like for use with the devices described above with reference to FIGS. 1-3. Control panel 565 may include sequencing module 545. The sequencing module 545 may provide communications with one or more electrodes 560 (also referred to as sensors or devices) directly or via other communication components, such as a transceiver 530 and/or antenna 535. The electrodes 560 may represent one or more of the electrodes 18, 20, or pairs of such electrodes in any of the embodiments described above. The sequencing module 545 may perform or control various operations associated with, for example, the electrodes 18, 20, controllers 22, or other components of the DNA sequencing devices and related systems as described above with reference to FIGS. 1-3.

Control panel 565 may also include a processor module 505, and memory 510 (including software/firmware code (SW) 515), an input/output controller module 520, a user interface module 525, a transceiver module 530, and one or more antennas 535 each of which may communicate, directly or indirectly, with one another (e.g., via one or more buses 540). The transceiver module 530 may communicate bi-directionally, via the one or more antennas 535, wired links, and/or wireless links, with one or more networks or remote devices. For example, the transceiver module 530 may communicate bi-directionally with one or more of device 550 and/or electrodes 560-a, 560-c. The device 550 may be components of the DNA sequencing devices and related systems and devices described with reference to FIGS. 1-3, or other devices in communication with such systems and devices. The transceiver 530 may include a modem to modulate the packets and provide the modulated packets to the one or more antennas 535 for transmission, and to demodulate packets received from the one or more antennas 535. In some embodiments (not shown) the transceiver may communicate bi-directionally with one or more of device 550, a remote control device, and/or electrodes 560-a, 560-c through a hardwired connection without necessarily using antenna 535. While a control panel or a control device (e.g., 565) may include a single antenna 535, the control panel or the control device may also have multiple antennas 535 capable of concurrently transmitting or receiving multiple wired and/or wireless transmissions. In some embodiments, one element of control panel 565 (e.g., one or more antennas 535, transceiver module 530, etc.) may provide a connection using wireless techniques, including digital cellular telephone connection, Cellular Digital Packet Data (CDPD) connection, digital satellite data connection, and/or another connection.

The signals associated with system 500 may include wireless communication signals such as radio frequency, electromagnetics, local area network (LAN), wide area network (WAN), virtual private network (VPN), wireless network (using 302.11, for example), 345 MHz, Z-WAVE®, cellular network (using 3G and/or LTE, for example), and/or other signals. The one or more antennas 535 and/or transceiver module 530 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 535 may receive signals or information specific and/or exclusive to itself. In other embodiments, each antenna 535 may receive signals or information not specific or exclusive to itself.

In some embodiments, one or more electrodes 560 (e.g., voltage, inductance, resistance, current, force, temperature, etc.) or devices 550 may connect to some element of system 500 via a network using one or more wired and/or wireless connections. In some embodiments, the user interface module 525 may include an audio device, such as an external speaker system, an external display device such as a display screen, and/or an input device (e.g., remote control device interfaced with the user interface module 525 directly and/or through I/O controller module 520).

One or more buses 540 may allow data communication between one or more elements of control panel 565 (e.g., processor module 505, memory 510, I/O controller module 520, user interface module 525, etc.).

The memory 510 may include random access memory (RAM), read only memory (ROM), flash RAM, and/or other types. The memory 510 may store computer-readable, computer-executable software/firmware code 515 including instructions that, when executed, cause the processor module 505 to perform various functions described in this disclosure (e.g., initiating an adjustment of a lighting system, etc.). Alternatively, the software/firmware code 515 may not be directly executable by the processor module 505 but may cause a computer (e.g., when compiled and executed) to perform functions described herein. Alternatively, the computer-readable, computer-executable software/firmware code 515 may not be directly executable by the processor module 505 but may be configured to cause a computer (e.g., when compiled and executed) to perform functions described herein. The processor module 505 may include an intelligent hardware device, e.g., a central processing unit (CPU), a microcontroller, an application-specific integrated circuit (ASIC), etc.

In some embodiments, the memory 510 can contain, among other things, the Basic Input-Output system (BIOS) which may control basic hardware and/or software operation such as the interaction with peripheral components or devices. For example, the sequencing module 545, and other modules and operational components of the control panel 565 used to implement the present systems and methods may be stored within the system memory 510. Applications resident with system 500 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 530, one or more antennas 535, etc.).

Many other devices and/or subsystems may be connected to one or may be included as one or more elements of system 500. In some embodiments, all of the elements shown in FIG. 7 need not be present to practice the present systems and methods. The devices and subsystems can be interconnected in different ways from that shown in FIG. 7. In some embodiments, an aspect of some operation of a system, such as that shown in FIG. 7, may be readily known in the art and are not discussed in detail in this application. Code to implement the present disclosure can be stored in a non-transitory computer-readable medium such as one or more of system memory 510 or other memory. The operating system provided on I/O controller module 520 may be iOS®, ANDROID®, MS-DOS®, MS-WINDOWS®, OS/2®, UNIX®, LINUX®, or another known operating system.

The transceiver module 530 may include a modem configured to modulate the packets and provide the modulated packets to the antennas 535 for transmission and/or to demodulate packets received from the antennas 535. While the control panel or control device (e.g., 505) may include a single antenna 535, the control panel or control device (e.g., 505) may have multiple antennas 535 capable of concurrently transmitting and/or receiving multiple wireless transmissions.

In some embodiments, the DNA sequencing device and systems described herein may be used to collect electronic signals associated with the nucleotides of a DNA strand passing through the gap between electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

While the examples disclosed herein are related to a four-letter DNA sequence, the principles disclosed herein may be applicable to other types of DNA strands with other numbers of nucleotides and/or types of nucleotides. The use of dyes and/or peptides to attach at specific sites/nucleotides of a given DNA strand may generally provide enhanced discrimination and/or identification of that particular type of nucleotide on any DNA or RNA strand.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

- U.S. Prov. App. No. 62/453,270, titled "SINGLE-MOLECULE DNA SEQUENCING METHOD USING CONFINED NANO-FLUIDIC CHANNEL AND SUB-NANOMETER ELECTRODE GAP," filed on 1 Feb. 2017, and U.S. patent application Ser. No. 15/886,442, titled "SINGLE-MOLECULE DNA SEQUENCING METHOD USING CONFINED NANO-FLUIDIC CHANNEL AND SUB-NANOMETER ELECTRODE GAP," filed on 1 Feb. 2018.
- U.S. Prov. App. No. 62/453,398, titled "NANOFLUIDIC CHANNEL OPENING SIZE CONTROL USING ACTUATION," filed on 1 Feb. 2017, and U.S. patent application Ser. No. 15/886,483, titled "NANOFLUIDIC CHANNEL OPENING SIZE CONTROL USING ACTUATION," filed on 1 Feb. 2018.
- U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.
- U.S. Prov. App. No. 62/453,307, titled "METHOD TO FABRICATE A NANOCHANNEL FOR DNA SEQUENCING BASED ON NARROW TRENCH PATTERNING PROCESS," filed on 1 Feb. 2017, and U.S. patent application Ser. No. 15/886,533, titled "METHOD TO FABRICATE A NANOCHANNEL FOR DNA SEQUENCING BASED ON NARROW TRENCH PATTERNING PROCESS," filed on 1 Feb. 2018.
- U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560, titled "FABRICATION OF A DEVICE FOR SINGLE-MOLECULE DNA SEQUENCING USING SIDEWALL LITHOGRAPHY," filed on 1 Feb. 2018.
- U.S. Prov. App. No. 62/453,339, titled "FABRICATION OF A NANOCHANNEL FOR DNA SEQUENCING USING ELECTRICAL PLATING TO ACHIEVE TUNNELING ELECTRODE GAP," filed on 1 Feb. 2017, and U.S. patent application Ser. No. 15/886,581, titled "FABRICATION OF A NANOCHANNEL FOR DNA SEQUENCING USING ELECTRICAL PLATING TO ACHIEVE TUNNELING ELECTRODE GAP," filed on 1 Feb. 2018.
- U.S. Prov. App. No. 62/453,346, titled "NANOSTRUCTURES TO CONTROL DNA STRAND ORIENTATION AND POSITION LOCATION FOR TRANSVERSE DNA SEQUENCING," filed on 1 Feb. 2017, and U.S. patent application Ser. No. 15/886,608, titled "NANOSTRUCTURES TO CONTROL DNA STRAND ORIENTATION AND POSITION LOCATION FOR TRANSVERSE DNA SEQUENCING," filed on 1 Feb. 2018.
- U.S. Prov. App. No. 62/453,365, titled "FABRICATION OF WEDGE SHAPED ELECTRODE FOR ENHANCED DNA SEQUENCING USING TUNNELING CURRENT," filed on 1 Feb. 2017, and U.S. patent application Ser. No. 15/886,661, titled "FABRICATION OF WEDGE SHAPED ELECTRODE FOR ENHANCED DNA SEQUENCING USING TUNNELING CURRENT," filed on 1 Feb. 2018.
- U.S. Prov. App. No. 62/453,329, titled "DIRECT SEQUENCING DEVICE WITH A TOP-BOTTOM ELECTRODE PAIR," filed on 1 Feb. 2017, and U.S. patent application Ser. No. 15/886,685, titled "DIRECT SEQUENCING DEVICE WITH A TOP-BOTTOM ELECTRODE PAIR," filed on 1 Feb. 2018.
- U.S. Prov. App. No. 62/453,376, titled "MICRO AND NANOFLUIDIC CHANNEL CONTROLLED ACTUATION TO OPEN CHANNEL GAP," filed on 1 Feb. 2017.
- U.S. Prov. App. No. 62/469,393, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2017, and U.S. patent application Ser. No. 15/886,736, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A method of forming a nanopore device for DNA sequencing, the method comprising:
    forming a first electrode member and a second electrode member on a substrate by depositing a conductive layer on the substrate and on a sacrificial channel deposit, the first and second electrode members being spaced apart by an electrode gap in the range of about 0.3 nm to about 2 nm and the sacrificial channel deposit defining the electrode gap;
    depositing an insulating layer over the first and second electrode members and the substrate;
    forming a nanopore through the insulating layer and the substrate in alignment with the electrode gap, the nanopore having an inlet opening along a top surface of the insulating layer.

2. The method of claim 1, wherein forming the first and second electrode members comprises using an evaporation technique.

3. The method of claim 1, comprising forming the electrode gap by depositing at least one sacrificial layer using at least one of sputter deposition, chemical vapor deposition, and atomic layer deposition, and then removing a portion of the sacrificial layer to form the sacrificial channel deposit.

4. The method of claim 1, wherein forming the nanopore includes drilling through the insulating layer and the substrate using a focused electron beam or focused ion beam technique.

5. The method of claim 1, wherein depositing the insulating layer includes depositing by isotropic deposition.

6. A method of forming a nanopore device for DNA sequencing, the method comprising:
    providing a first sacrificial layer on a substrate, the first sacrificial layer having an exposed sidewall on the substrate;
    providing a second sacrificial layer over the first sacrificial layer, the substrate, and the exposed sidewall;
    removing the second sacrificial layer from the first sacrificial layer and from the substrate and removing the first sacrificial layer from the substrate, while leaving the second sacrificial layer on the exposed sidewall forming a sacrificial channel deposit;
    forming a conductive coating on the substrate and the sacrificial channel deposit;
    removing the sacrificial channel deposit having the conductive coating thereon, leaving a first electrode member and a second electrode member on the substrate with an electrode gap between the first and second electrode members;
    depositing an insulating layer over the first and second electrode members and the electrode gap; and
    forming a nanopore through the insulating layer and the substrate in alignment with the electrode gap, the nanopore having an inlet opening along a top surface of the insulating layer.

7. The method of claim 6, wherein the electrode gap is in the range of about 0.3 nm to about 2 nm.

8. The method of claim 6, wherein forming the conductive coating comprises using an evaporation or sputter deposition technique.

9. The method of claim 6, wherein:
    providing the first sacrificial layer comprises depositing the first sacrificial layer using at least one of sputter deposition, chemical vapor deposition, and atomic layer deposition; and
    providing the second sacrificial layer comprises depositing the second sacrificial layer using at least one of sputter deposition, chemical vapor deposition, and atomic layer deposition.

10. The method of claim 6, wherein removing the sacrificial channel deposit having the conductive coating thereon comprises wet stripping.

11. The method of claim 6, wherein depositing the insulating layer includes depositing by isotropic deposition.

12. The method of claim 6, wherein forming the nanopore comprises drilling through the insulating layer and the substrate using a focused electron beam or focused ion beam technique.

13. A method of forming a nanopore device for DNA sequencing, the method comprising:
    providing a first sacrificial layer on a portion of a substrate, the first sacrificial layer having an exposed sidewall at the substrate;

providing a second sacrificial layer over the first sacrificial layer, the substrate, and the exposed sidewall;

removing the second sacrificial layer and the first sacrificial layer exposing the substrate and leaving a sacrificial channel deposit on the substrate;

forming a conductive coating on the exposed substrate and the sacrificial channel deposit;

removing the sacrificial channel deposit having the conductive coating thereon, leaving a first electrode member and a second electrode member with an electrode gap therebetween;

depositing an insulating layer over the first and second electrode members and the electrode gap; and forming a nanopore through the insulating layer and the substrate in alignment with the electrode gap, the nanopore having an inlet opening along a top surface of the insulating layer.

14. The method of claim 13, wherein the electrode gap is in the range of about 0.3 nm to about 2 nm.

15. The method of claim 13, wherein forming the conductive coating comprises using an evaporation or sputter deposition technique.

16. The method of claim 13, wherein:

providing the first sacrificial layer comprises depositing the first sacrificial layer using at least one of sputter deposition, chemical vapor deposition, and atomic layer deposition; and providing the second sacrificial layer comprises depositing the second sacrificial layer using at least one of sputter deposition, chemical vapor deposition, and atomic layer deposition.

17. The method of claim 13, wherein removing the sacrificial channel deposit having the conductive coating thereon comprises wet stripping.

18. The method of claim 13, wherein depositing the insulating layer comprises depositing by isotropic deposition.

19. The method of claim 13, wherein forming the nanopore comprises drilling through the insulating layer and the substrate using a focused electron beam or focused ion beam technique.

* * * * *